United States Patent [19]
Jones

[11] Patent Number: 5,900,067
[45] Date of Patent: May 4, 1999

[54] HANDWASHING TECHNIQUE ANALYSIS

[76] Inventor: C. Kerry Jones, 1347 Leeper, South Bend, Ind. 46617

[21] Appl. No.: 08/891,677

[22] Filed: Jul. 11, 1997

Related U.S. Application Data

[63] Continuation-in-part of application No. 08/441,823, May 16, 1995.

[51] Int. Cl.$^6$ ........................................................ B08B 7/00
[52] U.S. Cl. .................................. 134/1; 134/26; 134/29; 128/633; 252/301.16; 252/408.1
[58] Field of Search ..................................... 134/1, 26, 42, 134/29; 128/633; 252/408.1, 301.16

[56] References Cited

U.S. PATENT DOCUMENTS

| | | | |
|---|---|---|---|
| 3,640,889 | 2/1972 | Stewart | 252/301.2 R |
| 3,864,571 | 2/1975 | Stillman et al. | 250/302 |
| 4,610,806 | 9/1986 | Rosen | 252/301.16 |
| 4,623,579 | 11/1986 | Quon | 428/215 |
| 4,938,224 | 7/1990 | Rysavy | 128/633 |
| 4,965,063 | 10/1990 | Casey | 424/7.1 |
| 5,116,533 | 5/1992 | Grandmont et al. | 252/301.36 |
| 5,155,149 | 10/1992 | Atwater et al. | 524/88 |
| 5,498,280 | 3/1996 | Fistner et al. | 106/19 B |

OTHER PUBLICATIONS

Brochyre entitled "Glo Germ Can Help You Become a Germ Detective"!

Elaine Larson,"Hand Washing—It's Essential—Even If You Use Gloves", Journal of Nursing, Jul. 1989.

Bradley N. Doebbeling et al.,"Comparative Efficacy of Alternative Hand–Washing Agents in Reducing Noscomial Infections in Intensive Care Units", The New England Journal of Medicine, Jul. 9, 1992.

William M. Marcil,"Handwashing Practices Among Occupational Therapy Personnel", The American Journal of Occupational Therapy, vol. 47, No. 6, Jun. 1993.

Christopher Phillips,"Handy Hygiene", Nursing Times, vol. 85, No. 37, Sep. 13, 1989.

*Primary Examiner*—Harold Y. Pyon
*Attorney, Agent, or Firm*—Emrich & Dithmar

[57] ABSTRACT

A handwashing medium which may be in liquid, cream, powder or spray form is provided with a detection agent such as an invisible fluorescent or phosphorescent additive, which combination is then rubbed onto one's hands using the individual's handwashing technique. The individual's hands are rinsed with water as in the normal handwashing fashion and the hands are then exposed to an activating agent such as an ultraviolet (UV) light source where the invisible detection agent is fluorescent. Areas missed during handwashing retain the fluorescent additive and are clearly visible due to fluorescence. In the case of a phosphorescent detection agent, an ultraviolet light source is not necessary as the phosphorescent detection agent will emit light on its own without any external light source in a reduced light environment. The method is useful in evaluating one's handwashing technique and in the teaching of proper hygiene. The invisible fluorescent or phosphorescent additive in a handwashing medium may also be used in determining patterns of body part contact such as contact with one's hands or feet in a given area by applying the invisible fluorescent or phosphorescent additive to a body part and either exposing the area to UV light or viewing the area of interest in reduced light to detect the presence of residue of the fluorescent or phosphorescent agent. The use of a phosphorescent additive in the handwashing medium may also be used in determining patterns of body part contact by viewing the area of interest in reduced light.

10 Claims, 3 Drawing Sheets

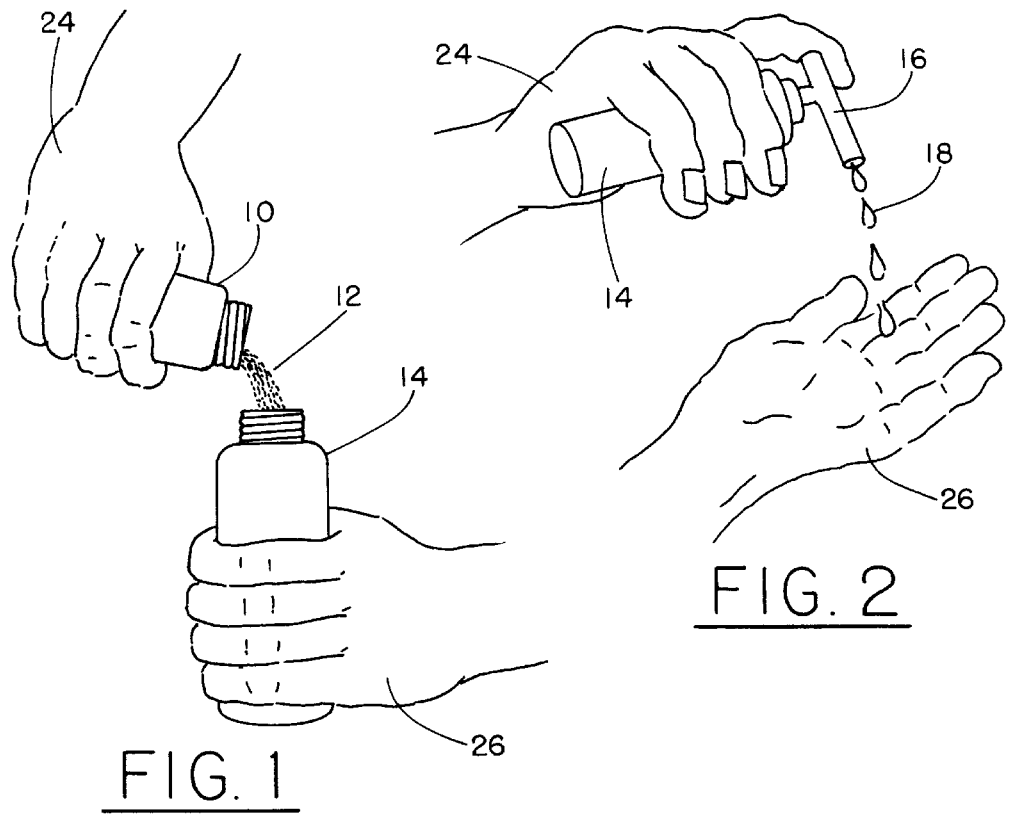
FIG. 1
FIG. 2
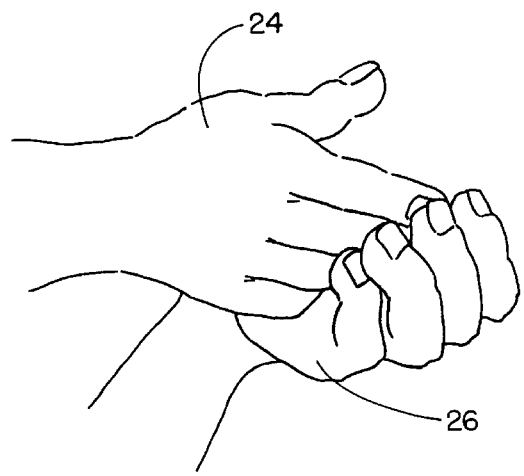
FIG. 3

HANDWASHING TECHNIQUE ANALYSIS

RELATED APPLICATION

This is a continuation-in-part of pending prior application Ser. No. 08/441,823, filed on May 16, 1995 for Handwashing Technique Analysis.

FIELD OF THE INVENTION

This invention relates generally to personal hygiene and is particularly directed to a method for evaluating the effectiveness of one's handwashing technique.

BACKGROUND OF THE INVENTION

Cleanliness is essential for good health. The spread of infectious disease has reached epidemic proportions in many parts of the world. Even in the more technically advanced countries, the increase in the spread of contagious diseases, which in many cases is fatal to the victim, has reached an alarming level and has caused great fear and anxiety. Because of the nature of human beings and the manner in which they interrelate, contagious disease and illness is frequently transmitted by hand. It has been determined that some organisms live for 150 minutes on the skin. Because many patients can be handled in a 2 ½ hour period, the risk of cross-infection is clearly great. The need for a high degree of cleanliness in certain environments such as hospitals, clinics, restaurants etc., is thus obvious. Great precautions are taken in these types of facilities to minimize the transfer of disease- causing microbes among people. In many cases, the transfer of disease is caused by improper cleaning such as of one's hands or by the improper or unauthorized handling of contaminated materials. Frequently, access to and the handling of contaminated materials or objects is inadvertent and the individual involved may not be aware that he or she has touched or been exposed to the source of contamination.

This invention addresses the aforementioned problems encountered in the prior art by providing a method which permits an individual to evaluate the effectiveness of his or her handwashing technique as well as to apprise the individual of his or her patterns of contact in a given area.

OBJECTS AND SUMMARY OF THE INVENTION

Accordingly, it is an object of the present invention to provide a method for evaluating the effectiveness of one's handwashing technique.

It is another object of the present invention to determine the extent of cleanliness of a body part after it has been washed.

Yet another object of the present invention is to instruct people, such as young children, in the area of personal hygiene and thus reduce the spread of infectious disease.

A further object of the present invention is to provide a simple, foolproof method for detecting contamination of a body part or object such as by accidental touching.

A still further object of the present invention is to provide information regarding one's contact pattern within a given area.

Another object of the present invention is to provide a handwashing medium which also permits the user to determine the effectiveness of his or her handwashing technique.

It is yet another object of the present invention to provide information regarding areas of human contact in an enclosed space such as a room by persons having access to the room for the purpose of tracking human contact patterns, developing cleaning strategies, or determining access of individuals to areas within the enclosed space.

The present contemplates a method for evaluating a person's handwashing technique comprising the steps of: adding an invisible detection agent to a soap or detergent based handwashing medium, wherein the invisible detection agent is phosphorescent; applying the handwashing medium containing the invisible phosphorescent detection agent to the person's hands; moving the person's hands into contact with one another in accordance with the handwashing technique of the person so as to spread the handwashing medium over both hands of the person; rinsing both hands in water so as to remove the handwashing medium from the hands; and viewing the person's hands in reduced light for determining the presence of any of the detection agent on the hands indicating an unwashed portion of the hands.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 1 is a simplified illustration of adding a detection agent such as fluorescent or phosphorescent powder to a container of handwashing lotion in accordance with one aspect of the present invention;

FIG. 2 is a simplified illustration of the dispensing of a handwashing lotion on one's hands in accordance with another aspect of the present invention;

FIG. 3 is a simplified illustration of the manner in which the handwashing lotion containing the fluorescent or phosphorescent powder is spread over one's hands in accordance with a typical handwashing technique;

DETAILED DESCRIPTION OF THE PREFERRED EMBODIMENTS

Figure 4:
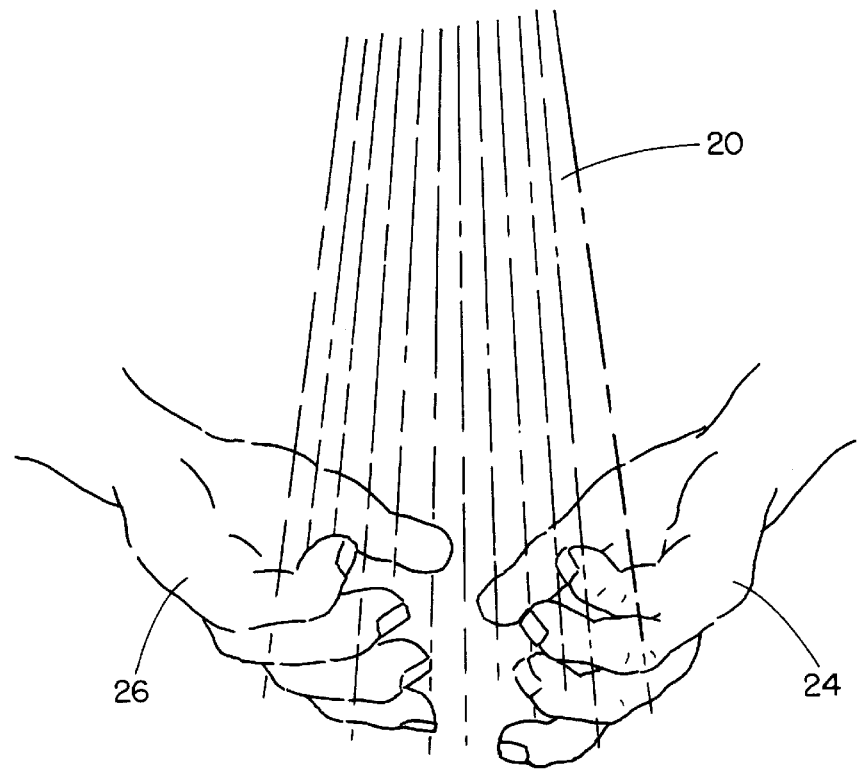
FIG. 4 is a simplified illustration of rinsing the handwashing lotion from the hands using a stream of water in accordance with another aspect of the present invention.

Referring to FIGS. 1–5, there is shown in simplified schematic diagram form the steps involved in carrying out the handwashing technique analysis of the present invention. The various figures illustrate a pair of hands on which the inventive handwashing technique analysis is applied, where the right and left hands are respectively identified by element numbers 24 and 26.

In FIG. 1, a fluorescent or phosphorescent powder 12 is shown being dispensed from a first container 10 into a second container 14 containing a handwashing medium. By handwashing medium is meant a conventional soap- or detergent-based cleansing agent. By fluorescent is meant the emission of electromagnetic (EM) radiation, especially visible light, resulting from absorption of incident radiation, which persists only as long as the stimulating incident radiation continues. By phosphorescence is meant the persistent emission of light following exposure to and removal of incident radiation. The emission of light occurs only during excitation in fluorescence, while in phosphorescent the emission of light continues after excitation. The fluorescent or phosphorescent agent may be in the form of a powder, as illustrated, a liquid, a cream or a spray. It is essential that the fluorescent or phosphorescent powder 12 be inconspicuous, or perhaps even invisible, so that when one applies the fluorescent or phosphorescent powder and a handwashing medium as described below to one's hands in a washing motion, the fluorescent or phosphorescent agent is essentially not visible during this handwashing process.

Referring to FIG. 2, the next step in the process is shown as applying the handwashing solution 18 from the second container 14 using a dispensing mechanism 16 onto one of the hands of the user. The handwashing medium 18 may also be in the form of a liquid, as illustrated, a cream, a powder or a spray, with any of the more conventional handwashing media adapted for use with the present invention. As shown in FIG. 2, the handwashing solution 18 is in the form of a series of drops deposited upon the user's left hand 26. FIG. 3 shows the user's right and left hands 24, 26 in engaging contact in a handwashing motion for distributing the handwashing solution containing the fluorescent or phosphorescent detection agent over both hands.

Figure 5:
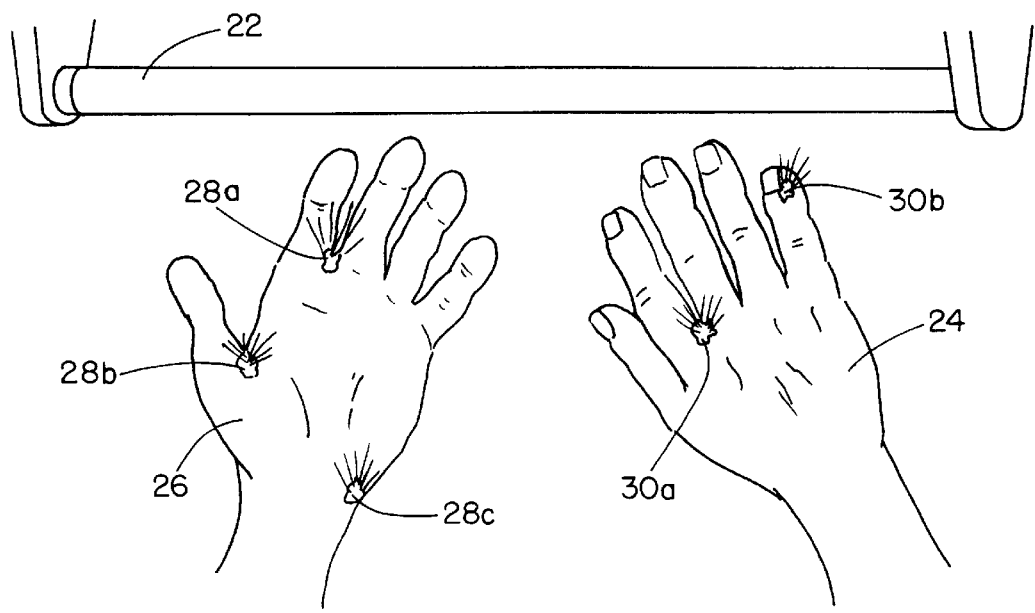
FIG. 5 is a simplified illustration of a pair of hands on which there remains a residue of fluorescent or phosphorescent powder following washing of the hands, where the residue may be activated by ultraviolet light for the case of a fluorescent residue or by the absence of ambient light for the case of a phosphorescent residue, and where in both cases the charged residue particles are visible on the body part.

The handwashing solution is then rinsed from the hands by means of a stream of water 20 as shown in FIG. 4. The water rinses the handwashing solution from the hands, leaving a residue of the fluorescent or phosphorescent agent on those portions of the hands which have not been exposed to and cleaned by the handwashing process. By irradiating hands 24 and 26 with an ultraviolet (UV) light source 22, the fluorescent residue is activated and readily visible in the form of fluorescent agent residue deposits 28a, 28b, and 28c on the left hand 26 and fluorescent agent residue deposits 30a and 30b on the right hand 24 as shown in FIG. 5. Areas where the fluorescent agent remains on the hands after rinsing of the handwashing solution indicates to the user those portions of the hands which have not been cleaned by the handwashing process. In this manner, the user can alter his or her handwashing technique to expose all surface portions of the hands to the handwashing solution for more effectively cleaning the hands. Where a phosphorescent agent is used, exposure of the washed hands to an activating agent is not required for viewing the essentially invisible detection agent. After the hands are washed using the invisible phosphorescent detection agent, the hands are then viewed under reduced light, or in a reduced light environment, for determining the presence of any of the detection agent indicating an unwashed portion of the hands. This embodiment of the invention has the advantage of eliminating the need for an activating agent such as a source of incident radiation on the hands during inspection of the hands following washing. This embodiment of the invention also offers increased flexibility and adaptability of the invention for use in various environments and facilities and affords accessibility of the present invention to a greater number of potential users.

Figure 6:
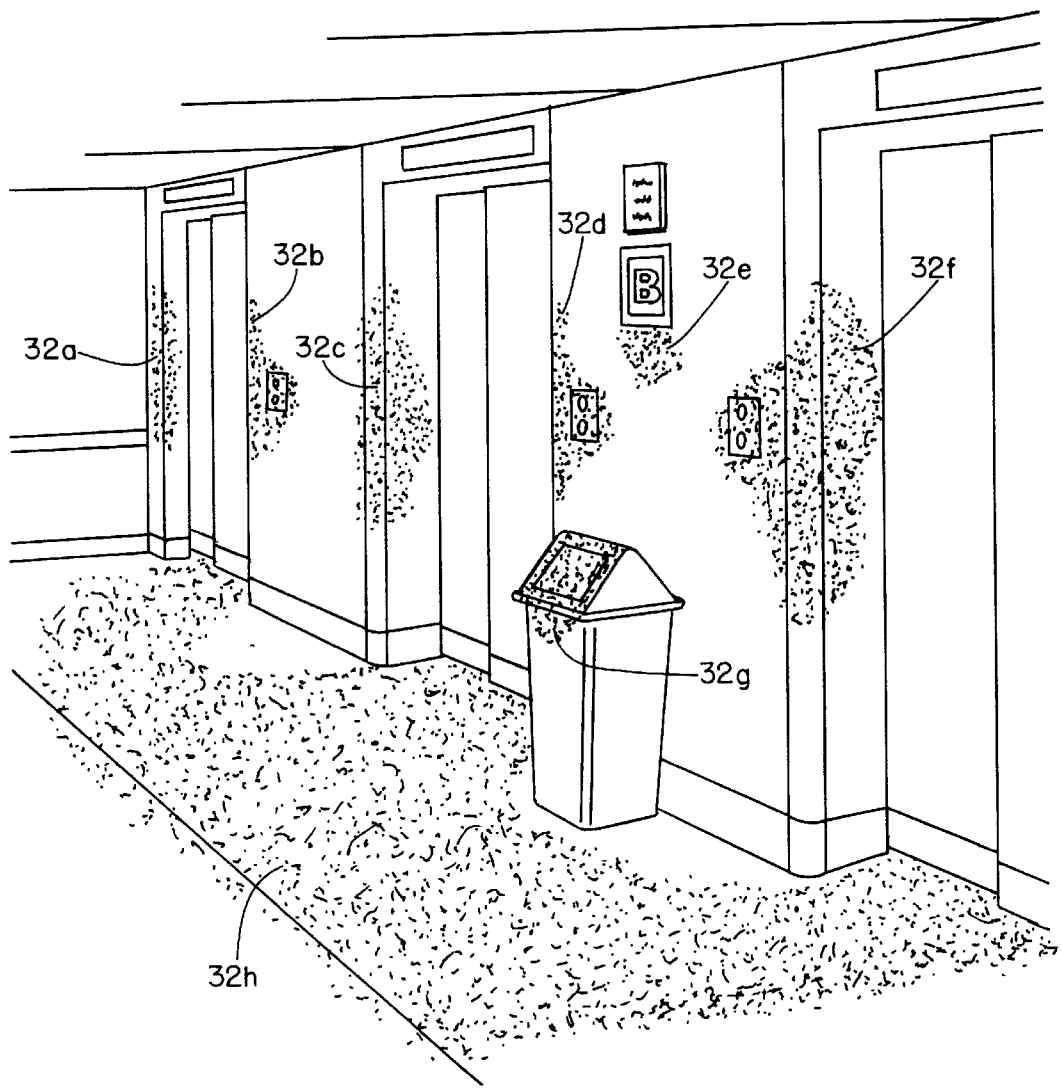
FIG. 6 is an illustration of a room on various portions of which there has been deposited a detection agent such as fluorescent or phosphorescent powder by contact by persons within the room in accordance with another aspect of the present invention.

Referring to FIG. 6, there is shown a space in which various areas have been marked by cross-hatching and are identified by element numbers 32a–32h. In accordance with another aspect of the invention, the invisible fluorescent or phosphorescent detection agent, may be applied to one's body parts, such as one's hands or feet, and during the course of carrying out one's activities in a given area, the body part comes in contact with areas 32a–32h within the space resulting in deposit of the fluorescent or phosphorescent detection agent on various surfaces within the space. Ultraviolet light, or other complementary activating agent, is then used to irradiate the space, activating the fluorescent agent deposited on various surfaces to indicate those surfaces upon which body contact has occurred. In the case of use of a phosphorescent agent, irradiation by an external light or other activation source is not necessary as the phosphorescent material serves as a persistent source of light in indicating those surfaces upon which body part contact has occurred. In this manner, those surfaces which are subject to frequent body part contact such as contact with the hands or feet of one or more individuals are indicated as areas for frequent and more intensive cleaning for improved hygiene and sanitation.

Another aspect of the invention contemplates applying the disclosed invisible detection agent to one or more locations in an enclosed space such as a room for the purpose of tracking human contact patterns with those locations to which the detection agent has been applied as well as with other locations in the room by those having access to the room. Determining body part contact with various portions of the room would assist in tracking contact patterns and in developing cleaning strategies. Determining access patterns would be useful in developing security measures and monitoring the activities of those having access to the room.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. A method for evaluating a person's handwashing technique comprising the steps of:

adding an invisible detection agent to a soap or detergent based handwashing medium, wherein said invisible detection agent is phosphorescent;

applying the handwashing medium containing the invisible phosphorescent detection agent to the person's hands;

moving the person's hands into contact with one another in accordance with the handwashing technique of the person so as to spread said handwashing medium over both hands of the person;

rinsing both hands in water so as to remove said handwashing medium from the hands; and viewing the person's hands in reduced light for determining the presence of any of said detection agent on the hands indicating an unwashed portion of the hands.

2. The method of claim 1 wherein said handwashing medium is in liquid, cream, powder or spray form.

3. The method of claim 2 wherein said detection agent is in liquid, cream, powder or spray form.

4. A method for indicating areas of body part contact on surface areas of a defined space such as a room, said method comprising the steps of:
   adding an invisible detection agent to a handwashing medium, wherein said invisible detection agent is phosphorescent;
   applying the invisible detection agent to a person's body part by washing the body part with said handwashing medium;
   allowing the person access to the defined space for the purpose of conducting activities therein; and
   observing the defined space in reduced light for determining the presence of said detection agent indicating contact of the washed body part with any portion of the defined space on which said detection agent is located.

5. The method of claim 4 wherein said handwashing medium is in liquid, cream, powder or spray form.

6. The method of claim 5 wherein said detection agent is in liquid, cream, powder or spray form.

7. A composition for washing one's hands and for indicating those portions of the hands which are not cleaned during the handwashing process, said composition comprising:
   a soap or detergent based hand washing agent for cleaning the hands when applied to the hands and rinsed away with a solvent such as water; and
   a phosphorescent detection agent disposed in said washing agent and generally invisible to the eye, wherein said phosphorescent detection agent remains on the hands after the hands are rinsed with water for indicating those portions of the hands which have not been cleaned during the handwashing process when viewed in reduced light.

8. The composition of claim 7 wherein said washing agent is in liquid, cream, powder or spray form.

9. The composition of claim 8 wherein said detection agent is in liquid, cream, powder or spray form.

10. A method of determining contact of various portions of an enclosure such as a room with body parts of persons within and moving about the room, said method comprising the steps of:
   applying an invisible phosphorescent detection agent to selected areas in the room;
   providing access to the room by persons conducting various activities in the room, wherein said invisible phosphorescent detection agent is spread from one of said selected areas by contact with a body part of a person in the room to another area of the room with which the body part comes in contact; and
   viewing the room in reduced light for rendering said phosphorescent detection agent visible for determining areas of body part contact other than said selected areas.

* * * * *